United States Patent [19]

Barrett et al.

[11] Patent Number: 5,099,067

[45] Date of Patent: Mar. 24, 1992

[54] USE OF AMMONIUM FORMATE AS A HYDROGEN TRANSFER REAGENT FOR REDUCTION OF CHIRAL NITRO COMPOUNDS WITH RETENTION OF CONFIGURATION

[75] Inventors: Anthony G. M. Barrett; Christopher D. Spilling, both of Evanston, Ill.

[73] Assignee: Northwestern University, Evanston, Ill.

[21] Appl. No.: 749,492

[22] Filed: Aug. 15, 1991

Related U.S. Application Data

[63] Continuation of Ser. No. 229,227, Aug. 5, 1988, abandoned.

[51] Int. Cl.$^5$ ............... C07C 211/08; C07C 211/16; C07C 211/27
[52] U.S. Cl. .................... 564/321; 564/416; 564/418; 564/357; 564/358; 564/448; 564/494; 564/495; 560/38; 560/39; 560/155; 560/160; 560/121; 560/123; 560/125; 562/443; 562/444; 562/567; 562/553; 562/507; 562/504; 562/506
[58] Field of Search ............... 564/416, 418, 321, 357, 564/358, 498, 494, 495; 560/38, 39, 155, 160, 121, 123, 125; 562/443, 444, 567, 553, 503, 504, 505, 506

[56] References Cited

U.S. PATENT DOCUMENTS

| | | | |
|---|---|---|---|
| 2,586,512 | 2/1918 | Burtner et al. | 568/704 |
| 3,651,144 | 3/1972 | Tindal | 568/704 |
| 3,883,580 | 5/1975 | Solodar | 568/704 |
| 3,968,147 | 7/1976 | Solodar | 568/704 |
| 4,067,905 | 1/1978 | Adrian et al. | 568/712 |
| 4,148,803 | 4/1979 | Whermeister | 564/401 |
| 4,448,999 | 3/1984 | Thewalt et al. | 564/495 |
| 4,746,737 | 5/1988 | Fujii et al. | 540/575 |

OTHER PUBLICATIONS

F. A. Carey, and Sandberg, R. J., "Advanced Organic Chemistry," 2nd ed. pp. 193–198, 1983, Plenum Press, New York.
Ram and Ehrenkaufer, *Tetrahedron Lett.*, 25:3415–3418 (1984).
Ram and Ehrenkaufer, *Synthesis*, Feb. 1988, pp. 91–95.
Ram and Ehrenkaufer, *Communications*, Feb. 1986, pp. 133–135.
Brieger and Nestrick, *Chem. Reviews*, 74:567–580 (1974).

*Primary Examiner*—Glennon H. Hollrah
*Assistant Examiner*—Mack W. Russell
*Attorney, Agent, or Firm*—Tilton, Fallon, Lungmus & Chestnut

[57] ABSTRACT

The present invention relates to a method of converting $\beta$-nitro compounds, specifically alcohols, into the corresponding hydroxy amines with retention of configuration by the use of ammonium formate.

15 Claims, 1 Drawing Sheet

USE OF AMMONIUM FORMATE AS A HYDROGEN TRANSFER REAGENT FOR REDUCTION OF CHIRAL NITRO COMPOUNDS WITH RETENTION OF CONFIGURATION

This application is a continuation of U.S. Ser. No. 229,227, filed Aug. 5, 1988, now abandoned.

BACKGROUND OF THE INVENTION

In 1984, Ram and Ehrenkaufer, Tetrahedron Lett. 1984, 25, 3415, reported that nitro compounds could be easily converted into the corresponding amines by transfer hydrogenation using ammonium formate catalyzed by palladium on carbon. The preparation of ammonium formate was described in 1941 by S. Zuffanti in J. Am. Chem. Soc. 1941, 63, 3123. It has been generally used in the precipitation of base metals from the salts of the noble metals. The use of ammonium formate in organic synthesis was first illustrated by Leucart in Ber-Disch. Chem. Ges. 1885, 18, 2341, in which various carbonyl compounds were reacted with ammonium formate to afford the corresponding amines. This process was later named as the "Leucart Reaction".

Ram et al. Tetrahedron Letter, supra, and Ram et al. Synthesis, 1986, 138, disclose the conversion of nitro compounds to the corresponding amines by transfer hydrogenation using ammonium formate in the presence of a palladium on carbon catalyst without concern directed to steric configuration. Reduction of nitro compounds to the corresponding amine has been generally thought, by those skilled in the art, to entail the loss of stereo configuration and production of racemic mixtures when the starting nitro compound is an enantiomercially pure material. This involved deprotonation of untreated nitro compound to form a nitronate anion which is planar and, therefore, one which forms a racemic mixture of nitro compound on reprotonation (an equilibrium reaction). The reduction of the thus formed reprotonated racemic nitro compound provides the corresponding racemic amino compound.

Conventional prior art processes for converting β-nitro alcohols into the corresponding hydroxy amines with retention of configuration were usually carried out by hydrogenation over Raney nickel or platinum catalysts. These procedures frequently required elevated temperatures and pressures and cannot be carried out at room temperature in a relatively mild procedure.

The present invention is directed to an improvement in the prior art process wherein the reduction protocol is clearly demonstrated to show that the ammonium formate transfer hydrogenation method is stereospecific and provides retention of configuration to the amines produced from functionalized nitro compounds as shown in FIG. I.

SUMMARY OF THE INVENTION

The present invention relates to a relatively simple method of converting chiral compounds, i.e., nitro compounds and preferably nitro alcohols, into amines by transfer hydrogenation wherein the configuration is retained. The stereospecific method comprises admixing a solution of the nitro compound with a catalyst followed by an excess of ammonium formate. The admixture is stirred at ambient temperature until the nitro compound is consumed. The amine is then separated.

More particularly, a preferred method comprises admixing a solution of nitro alcohol in THF and methanol with a 10% palladium on carbon catalyst followed by the admixture of excess ammonium formate in the amount of about 5 equivalents. The mixture is stirred at room temperature until the starting nitro alcohol has been consumed. The mixture is then diluted with $Et_2O$, filtered and the filtrate is evaporated in vacuo to yield the crude amine. Relative proportions of ammonium formate to the nitro compound range from about 3:1 to about 7:1.

DETAILED DESCRIPTION OF THE INVENTION

Figure 1:
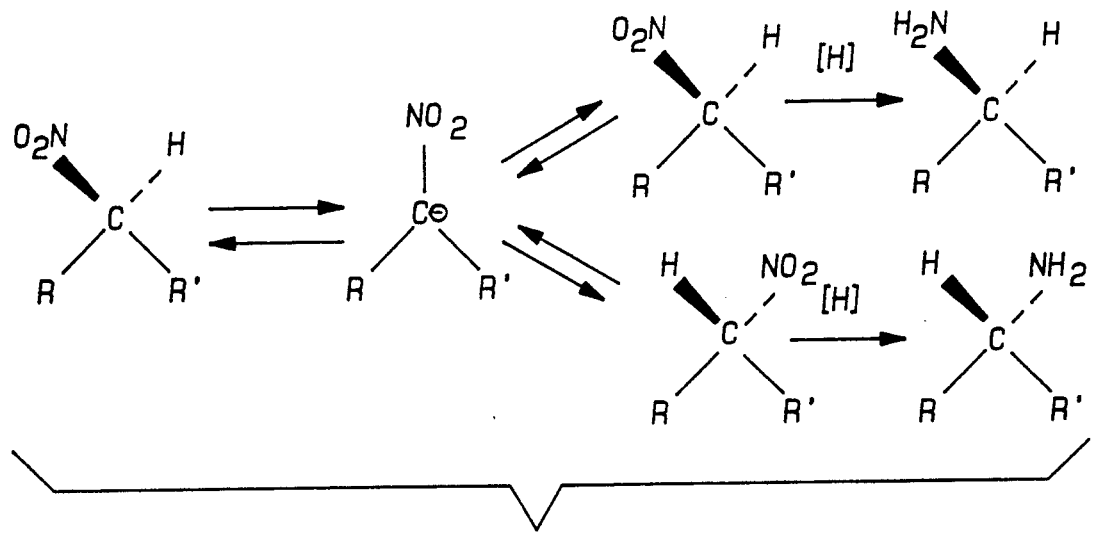
Figure 2:
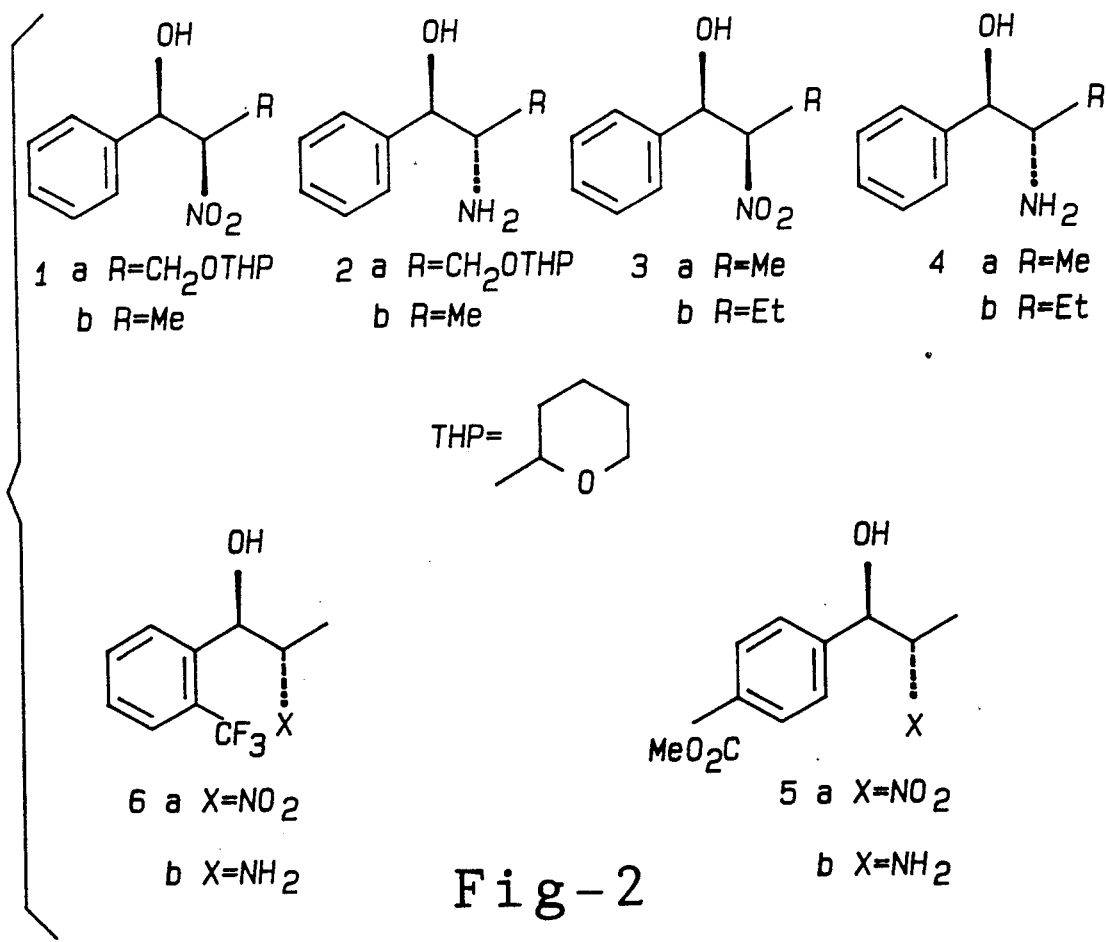

The method of the present invention is generally directed to the reduction of chiral nitro compounds to amines wherein chirality is retained by the use of ammonium formate as a hydrogen transfer reagent. Nitro compounds can be reduced to amines with retention of stereo configuration by the process of the present invention provided the carbon atom to which the nitro group is attached also has a hydrogen atom bonded to it.

In accordance with the present invention, the term "nitro compound" is defined as follows:

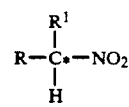

wherein R and $R^1$ are different and represent an unsubstituted or substituted alkyl, cycloalkyl or aryl group with the substitution being inert to the present reduction. The substituents may be ether, aryl, hydroxyl, carboxylic acid, ester groups and the like, the length of the carbon chain is immaterial, however, it is preferably 1-30 carbon atoms. While the present invention is generally directed to nitro compounds, it is specifically directed to chiral nitro alcohols without limitation.

"Nitro alcohol" refers to the following compound:

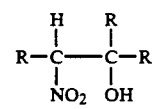

wherein each R can be the same or different, and represent the same groups as described above for R and $R^1$ for the nitro compound described above.

Nitro alcohols are frequently used as intermediates in the synthesis of β-amino alcohol derivatives; for example, they are useful in the synthesis of chloramphenicol, T. Controulis, et al., J. Am. Chem. Soc. 1949, 71, 2463, and of ephedrine, F. Hoover, et al., J. Org. Chem. 1967, 12, 506, and norephedrine.

Referring to FIG. II, the transfer hydrogenation of pure racemic threo nitro alcohol 1a in methanol solution produces the amino alcohol 2a with a yield of 80%. None of the erythro isomer is detected in such a product by NMR spectroscopy. In a similar manner, the nitro alcohols 1b (threo:erythro 6.5:1), 3a (threo:erythro 1:2.9), 3b (threo:erythro 1:3.2), 5a (erythro only) and 6a (threo:erythro 1:8.1) were converted into the corresponding β-amino alcohols 2b (44%, threo:erythro 6:1), 4a (61%, threo:erythro 1:2.8), 4b (87%, threo:erythro 1:3.2), 5b (73%, erythro) and 6b (58%, threo).

The method of the present invention relates to the use of ammonium formate as a hydrogen transfer reagent to convert chiral nitro compounds to amines wherein the same optical activity is retained in the resultant amine product. The ammonium formate is admixed in a solvent, which for purposes of this invention, may be any solvent capable of dissolving the ammonium formate and nitro compounds and be inert to the reaction conditions. Preferably, alcohol solvents are employed, such as methanol, ethanol, isopropyl alcohols, butanol and co-solvents such as diethyl ether, dimethyl ether, etc. Into this solvent the nitro compound is added. If the nitro compound is a nitro alcohol, it may be utilized as the solvent system. Further, a catalyst is added to the solvent. The catalyst may be any conventional hydrogenation-dehydrogenation catalyst. These conventional catalysts include, for example, catalysts supported by noble metals such as ruthenium, palladium or rhodium. Supports may include carbon, clay, aluminum, silica, etc. Preferably, a supported metal and palladium on carbon are utilized in catalytic amounts as a catalyst.

An excess of ammonium formate is utilized in the solvent over the amount of nitro compound. Equivalent amounts ranging from about 3:1 to about 7:1 of ammonium formate to nitro compound can be utilized. A preferred ratio is about 5:1.

After the catalyst, nitro compound and ammonium formate are added to the solvent, the mixture is stirred at a temperature effective to allow the nitro compound to be consumed. The effective reaction temperature may be from about 10° C. to about 100° C. Preferably, ambient temperature is utilized, however, higher temperatures may be used depending upon the boiling point of the solvent. Lower temperatures may also be utilized.

The reaction mixture may then be diluted with any suitable solvent, filtered and evaporated to recover the crude amine. Vacuum evaporation is preferred. Any conventional separation means may be utilized to purify the crude amine such as distillation, crystallization or chromatographic separation.

A typical procedure for converting nitro compounds into amines with retention of configuration comprises adding 10% palladium on carbon (50 milligram) to a solution of nitro alcohol (Scheme II, 3$b$) (0.219 grams, 1.1 mmol.) in THF and methanol (50:50, 10 mL) followed by the addition of an excess of ammonium formate (0.35 grams, 5 equiv.). The mixture is then stirred at room temperature until all the starting nitro alcohol has been consumed. The mixture is then diluted with Et$_2$O (100 mL), filtered, and the filtrate is evaporated in vacuo to yield the crude amine. Flash column chromatography (SiO$_2$, methanol chloroform, 2:98 v/v) yielded the amine 4$b$ (0.16 grams, 87%).

The method of the present invention is a relatively mild procedure for the conversion of the $\beta$-nitro alcohols into the corresponding hydroxy amines with retention of configuration.

In order to illustrate the method of converting the nitro alkanes to the corresponding amines with retention of configuration by transfer hydrogenation using ammonium formate, reference is made to the following examples which are, however, not to be interpreted as limiting the scope of this invention in any respect.

EXAMPLE 1

Reduction of Threo 1-Phenyl-2-Nitro-Propan-1-ol

To a solution of threo 1-phenyl-2-nitro-propan-1-ol (0.61 g, 0.0037 moles) in methanol (10 ml), was added 10% palladium on carbon (0.3 g) followed by ammonium formate (1.06 g, 5 equivalents). The resulting mixture was stirred for 1 hour then poured into Et$_2$O (200 mL) and filtered. The ether solution was washed with 0.1 M sodium hydroxide (50 mL), dried and evaporated in vacuo. The residue was taken up in Et$_2$O and treated with 2 mL of saturated HCl in Et$_2$O giving the crystalline hydrochloride salt (0.27 g, 44%).

EXAMPLE 2

Reduction of 3$\beta$-Acetoxy-6$\beta$-nitro-5$\alpha$-cholestane

To a solution of 3$\beta$-acetoxy-6$\beta$-nitro-5$\alpha$-cholestane (0.474 g, 0.001 mole) in THF (5 mL) and methanol (5 mL) was added 10% palladium on carbon (50 mg) followed by ammonium formate (0.315 g, 5 equivalents). The resulting mixture was stirred at room temperature for 50 minutes then diluted with Et$_2$O, filtered and evaporated in vacuo. Flash column chromatography (SiO$_2$, 4:1, hexane:Et$_2$O) gave 3$\beta$-acetoxy-6$\beta$-amino-5$\alpha$-cholestane (0.366 g, 82%).

EXAMPLE 3

Reduction of erythro 1-(2-trifluoromethylphenyl)-2-nitro-butan-1-ol

To a solution of etythro 1-(2-trifluoromethylphenyl)-2-nitro-butan-1-ol (0.18 g, 0.00068 mole) in THF (5 mL) and methanol (5 mL) was added 10% palladium on carbon (50 mg) followed by ammonium formate (0.21 g, 5 equivalents). The resulting mixture was stirred at room temperature for 1.5 hour then diluted with Et$_2$O, filtered and evaporated in vacuo. Flash column chromatography (SiO$_2$, 2% MeOH in CHCl$_3$) gave erythro 1-(2-trifluoromethylphenyl)-2-amino-butan-1-ol. (0.074 g, 47%), and some starting material (0.035 g).

EXAMPLE 4

Reduction of erythro 1-(4-methoxycarbonylphenyl)-2-nitro-butan-2-ol

To a solution of 1-(4-methoxycarbonylphenyl)-2-nitro-butan-2-ol (0.34 g, 1.3 mmol) in THF (5 mL) and methanol (5 mL) was added 10% palladium on carbon (50 mg) followed by ammonium formate (0.4 g, 5 equivalents). The resulting mixture was stirred at room temperature for 3 hours ten diluted with Et$_2$O, filtered and evaporated in vacuo. Flash column chromatography (SiO$_2$, 15% MeOH in CHCl$_3$) gave erythro 1-(4-methoxycarbonylphenyl)-2-amino-butan-1-ol (0.22 g, 73%).

We claim:

1. The method of reducing chiral nitro compounds while maintaining their configuration, comprising: admixing a catalyst with the nitro compound having a known optical purity greater than 0% and up to and including 100% in a solvent; admixing and stirring an excess of ammonium formate with said mixture converting the nitro compound to an amino while retaining the same optical purity of the compound; and separating the amine having the same configuration as the nitro compound.

2. The method of claim 1 wherein the nitro compound is a nitro alcohol.

3. The method of claim 1 wherein the ammonium formate and nitro compound are admixed in the ratio of about 7 to 1.

4. The method of claim 1 wherein the ammonium formate and nitro compound are admixed in the ratio of about 5 to 1.

5. The method of claim 1 wherein the ammonium formate and nitro compound are admixed in ratios ranging from 3:1 to 7:1.

6. The method of claim 1 wherein the catalyst is palladium on carbon.

7. The method of claim 1 wherein the solvent is any solvent capable of dissolving ammonium formate and the nitro compound.

8. The method of claim 1 wherein the temperature is about 10° C. to about 100° C.

9. The method of reducing chiral nitro alcohols while maintaining their configuration, comprising: admixing a catalyst with the nitro alcohol having a known optical purity greater than 0% and up to and including 100%; admixing and stirring an excess of ammonium formate with said mixture; converting the nitro alcohol to an amine alcohol while retaining the same optical purity of the alcohol and separating the amine having the same configuration as the nitro compound.

10. The method of claim 9 wherein the ammonium formate and nitro alcohol are admixed in the ratio of about 7 to 1.

11. The method of claim 9 wherein the ammonium formate and nitro alcohol are admixed in the ratio of about 5 to 1.

12. The method of claim 9 wherein the ammonium formate and nitro alcohol are admixed in ratios ranging from 3:1 to 7:1.

13. The method of claim 9 wherein the catalyst is palladium on carbon.

14. The method of claim 9 wherein the solvent is any solvent capable of dissolving ammonium formate and the nitro alcohol.

15. The method of claim 9 wherein the temperature is about 10° C. to about 100° C.

* * * * *